(12) United States Patent
Chavez et al.

(10) Patent No.: US 9,074,199 B1
(45) Date of Patent: Jul. 7, 2015

(54) MUTANT CAS9 PROTEINS

(71) Applicant: President and Fellows of Harvard College, Cambridge, MA (US)

(72) Inventors: Alejandro Chavez, Brookline, MA (US); Frank Poelwijk, Dallas, TX (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/319,784

(22) Filed: Jun. 30, 2014

Related U.S. Application Data

(60) Provisional application No. 61/906,374, filed on Nov. 19, 2013.

(51) Int. Cl.
*C12N 9/22* (2006.01)

(52) U.S. Cl.
CPC ........................................ *C12N 9/22* (2013.01)

(58) Field of Classification Search
CPC .............................................. C12Y 301/26012
USPC ......................................................... 435/199
See application file for complete search history.

(56) References Cited

U.S. PATENT DOCUMENTS

| | | | |
|---|---|---|---|
| 8,697,359 | B1 | 4/2014 | Zhang |
| 2010/0076057 | A1 | 3/2010 | Sontheimer et al. |
| 2011/0189776 | A1 | 8/2011 | Terns et al. |
| 2011/0223638 | A1 | 9/2011 | Wiedenheft et al. |
| 2011/0286980 | A1 | 11/2011 | Brenner |
| 2013/0130248 | A1 | 5/2013 | Haurwitz et al. |
| 2013/0253040 | A1 | 9/2013 | Miller et al. |
| 2014/0242700 | A1 | 8/2014 | Zhang et al. |
| 2014/0273226 | A1* | 9/2014 | Wu .............................. 435/455 |

FOREIGN PATENT DOCUMENTS

| | | |
|---|---|---|
| WO | 2008/108989 | 9/2008 |
| WO | 2010/054108 | 5/2010 |
| WO | 2011/143124 | 11/2011 |
| WO | 2012/164565 | 12/2012 |
| WO | 2013/098244 | 7/2013 |
| WO | 2013/126794 A1 | 8/2013 |
| WO | 2013/141680 A1 | 9/2013 |
| WO | 2013/142578 A1 | 9/2013 |
| WO | 2013/176772 | 11/2013 |
| WO | 2014/022702 A2 | 2/2014 |

OTHER PUBLICATIONS

Al-Attar et a!., Clustered Regularly Interspaced Short Palindromic Repeats (CRISPRs ): The Hallmark of an Ingenious Antiviral Defense Mechanism in Prokaryotes, Bioi Chern. (20 11) vol. 392, Issue 4, pp. 277-289.
Carroll, "A CRISPR Approach to Gene Targeting" 20(9) Molecular Therapy 1658-1660 (Sep. 2012).
Gasiunas eta!., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012).
Jinek et aL., "A Programmable Dual-RNA-Guided DNA Endonuclease in Adaptive Bacterial Immunity" 337 Science 816-821 (Aug. 17, 2012).
Jinek , et al. 'RNA-programmed genome editing in human cells.' eLite 2013;2:e00471 . [retrieved 1-3, 6, 7, 10-12 on Jun. 3, 2014). Retrieved from the Internet. <URL: http://elife .elifesciences.org/content/2/e00471 >. entire document.
Hale et al., Essential Features and Rational Design of CRISPR RNAs That Function With the Cas RAMP Module Complex to Cleave RNAs, Molecular Cell, (20 12) vol. 45, Issue 3, 292-302.
Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.
Makarova et al., "Evolution and classification of the CRISPR-Cas systems" 9(6) Nature Reviews Microbiology 467-477 (1-23) (Jun. 2011).
Roh et al. 'Diverse CRISPRs Evolving in Human Microbiomes.' PLoS Genetics. vol. 8, No. 6. 1-14 pp. 1-12. Jun. 2012. entire document.
Sontheimer Erik, Project 7: Establishing RNA-Directed DNA Targeting in Eukaryotic Cells; Project dates: Nov. 16, 2011 to Dec. 31, 2012 (Feb. 4, 2012).
Wiedenheft eta!., "RNA-guided genetic silencing systems in bacteria and archaea" 482 Nature 331-338 (Feb. 16, 2012).
International Search Report issued from corresponding PCT/US2014/066375, dated Apr. 17, 2015.
Chylinski et al. The tracrRNA and Cas9 families of type II CRJSPR-Cas immunity systems. RNA Bioi May 2013 vol. 10 No. 5 pp. 726-737. Especially 727 col. 1 para 1, p. 727 col. 2 para 2, Suppl Fig S1.
Esvel T et al. Orthogonal Cas9 proteins for RNA-guided gene regulation and editing. Nature Methods Epub Sep. 29, 2013 vol. 10 No. 11 pp. 1116-1121. Especially p. 1 col. 2 para 4.
Mali et al. CAS9 transcriptional activators for target specificity screening and paired nickases for cooperative genome engineering. Nature Biotechnology ePub Aug. 1, 2013 vol. 31 No. 9 pp. 833-838. Especially p. 5 para 4, Suppl Fig S15.
Van Leeuwen et al. Linker length and composition influence the flexibility of Oct-1 DNA binding. EMBO J Apr. 15, 1997 vol. 12043-2053. Especially abstract, p. 2043 col. 2 para 2, p. 2044fig 1B.
Zhou et al. Alteration of substrate specificities of thermophilic alpha/beta hydrolases through domain swapping and domain interface optimization. Acta Biochim Biophys Sin Dec. 2012 Vo144 No. 12 pp. 965-973. Especially abstract.

* cited by examiner

*Primary Examiner* — Tekchand Saidha
(74) *Attorney, Agent, or Firm* — Banner & Witcoff, Ltd.

(57) ABSTRACT

Methods of making mutant Cas9 proteins are described.

9 Claims, 1 Drawing Sheet

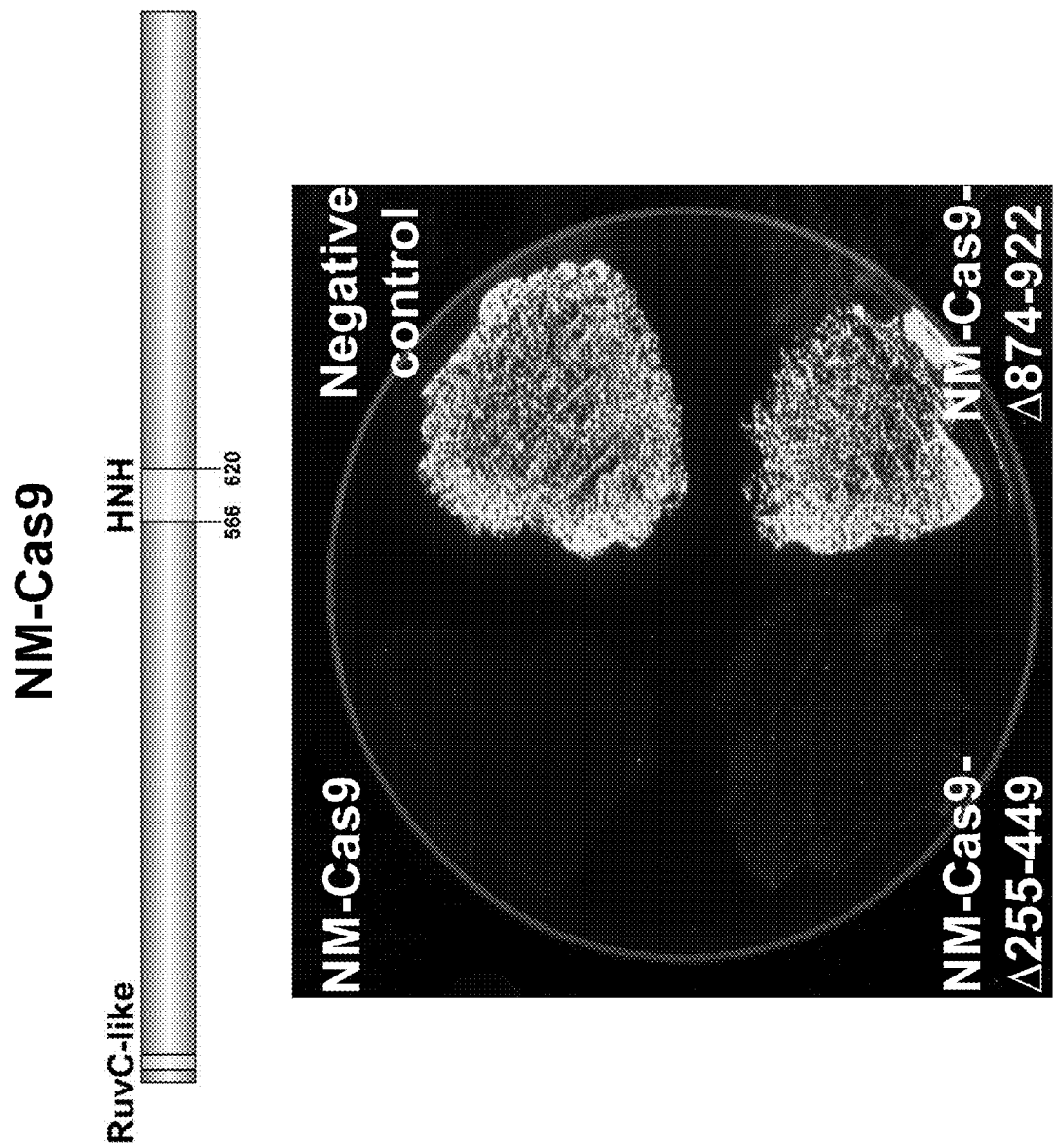

MUTANT CAS9 PROTEINS

RELATED APPLICATION DATA

This application claims priority to U.S. Provisional Patent Application No. 61/906,374 filed on Nov. 19, 2013 and is hereby incorporated herein by reference in its entirety for all purposes.

STATEMENT OF GOVERNMENT INTERESTS

This invention was made with government support under Grant No. P50 HG005550 awarded by the National Institutes of Health. The government has certain rights in the invention.

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

Cas9 is a DNA nuclease that can be programmed to target nearly any region of a genome by expressing a guide RNA (gRNA) that contains a motif that recruits Cas9 and 20 basepairs of complementarity to a region of the genome where targeting is desired. All characterized and putative Cas9 family members are several kilobases in size (>3,000 basepairs) with the smallest functionally validated member NM-Cas9 (*Neisseria meningitides* Cas9) being 3,249 basepairs in size. The large size of this protein limits its potential for biotechnology and therapeutic applications due to difficulties of delivery and manipulation.

SUMMARY

Aspects of the present disclosure are directed to an RNA guided DNA binding protein of a Type II CRISPR System that binds to the DNA and is guided by the one or more RNAs which has been engineered to omit portions of the protein while still functioning as an RNA guided DNA binding nuclease that can bind to target DNA and create a double stranded break in target DNA. According to one aspect, the RNA guided DNA binding protein of a Type II CRISPR System is a Cas9 protein.

Aspects of the present disclosure are directed to an RNA guided DNA binding protein of a Type II CRISPR System which has been engineered to omit portions of the protein while still functioning as an RNA guided DNA binding nickase that can bind to target DNA and create a single stranded break or nick in target DNA. According to one aspect, the RNA guided DNA binding protein of a Type II CRISPR System is a Cas9 protein.

Aspects of the present disclosure are directed to an RNA guided DNA binding protein of a Type II CRISPR System which has been engineered to omit portions of the protein while still functioning as an RNA guided DNA binding protein which is nuclease null, that is, the RNA guided DNA binding protein lacks nuclease activity. According to one aspect, the RNA guided DNA binding protein of a Type II CRISPR System is a Cas9 protein.

According to one aspect, portions of an RNA guided DNA binding protein are identified for deletion by identifying within a population of species of the RNA guided DNA binding protein sequences which are not well conserved or are otherwise highly divergent within a particular RNA guided DNA binding protein family. In order to identify sequences which are not well conserved within the context of this disclosure, an alignment was obtained from PFAM or otherwise created from a collection of sequences resulting from a database search of Cas9 homologs. This alignment was computationally conditioned and the conservation was calculated as the per position (relative) entropy of amino acid frequencies. The sequences are then removed from the RNA guided DNA binding protein to produce a mutant.

According to certain aspects, the present disclosure describes synthetic NM-Cas9 deletion mutants that are smaller in size yet retain near wild-type protein activity. The synthetic NM-Cas9 deletion mutants can be used to bind to DNA as a co-localization complex with guide RNA in a cell and create a double stranded break, a single stranded break or to locate an effector group near target DNA of interest to perform a desired function.

According to one aspect, the cell is a prokaryotic cell or a eukaryotic cell. According to one aspect, the cell is a bacterial cell, a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the one or more RNAs is a guide RNA. According to one aspect, the one or more RNAs is a crRNA. According to one aspect, the one or more RNAs is a tracrRNA. According to one aspect, the one or more RNAs is a tracrRNA-crRNA fusion.

According to one aspect, the target DNA is genomic DNA, mitochondrial DNA, viral DNA, conjugatable element or exogenous DNA.

According to one aspect, the RNA guided DNA binding protein is of a Type II CRISPR System that binds to the DNA and is guided by the one or more RNAs. According to one aspect, the RNA guided DNA binding protein is a Cas9 protein that binds to the DNA and is guided by the one or more RNAs.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1 is an image in which *E. coli* cells contain a YFP reporter for NM-Cas9 activity and are transformed with various NM-Cas9 nuclease null genes. In the absence of NM-Cas9, the cells are fluorescent (upper right quadrant-Negative control) and in the presence of full length nuclease null NM-Cas9 the cells are non-fluorescent (upper left quadrant-Positive control). Two of the generated NM-Cas9 deletions are shown, NM-Cas9-Δ255-449 shows near wild-type levels of repression (bottom left quadrant) and NM-Cas9-Δ874-922 shows lack of most DNA binding capacity (bottom right quadrant).

DETAILED DESCRIPTION

Embodiments of the present invention are directed to mutant RNA guided DNA binding proteins of the Type II CRISPR system. Such mutants are created by removing sequences that are not well conserved or are otherwise highly divergent among species within a genus of RNA guided DNA binding proteins of the Type II CRISPR system. According to one aspect, the sequences of species within a family of RNA guided DNA binding proteins are aligned and sequences of low conservation are determined. These sequences are then deleted from a particular RNA guided DNA binding protein. Exemplary RNA guided DNA binding proteins include Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477. The mutant DNA binding proteins described herein can be used to make double stranded cuts in target DNA, single stranded cuts in target DNA or to bind to target DNA in a manner to locate an effector group near the target DNA such that that effector group can interact with the target DNA. Such effector groups include activators or repressors known to those of skill in the art.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein of a Type II CRISPR System. An exemplary DNA binding protein is a Cas9 protein.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., *Science* 337, 816-821 (2012) hereby incorporated by reference in its entirety. Cas9 proteins are known to exist in many Type II CRISPR systems including the following as identified in the supplementary information to Makarova et al., *Nature Reviews, Microbiology*, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio sal-*

*exigens* DSM 2638; *Campylobacter jejuni doylei* 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a mutant of a Cas9 protein present in a Type II CRISPR system, such as any one of the species identified above. An exemplary Cas9 protein is that found in *Neisseria meningitides*, such as *Neisseria meningitides* 053442; *Neisseria meningitides* alpha14; *Neisseria meningitides* Z2491.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Particular cells include stem cells, such as pluripotent stem cells, such as human induced pluripotent stem cells.

Target nucleic acids include any nucleic acid sequence to which a mutant RNA guided DNA binding protein nuclease can be useful to nick or cut. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and mutant Cas9 proteins which co-localize to a DNA including a target nucleic acid. DNA includes genomic DNA, mitochondrial DNA, viral DNA, a conjugatable element or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

According to one aspect, the genetic material required to encode a Cas9 protein is reduced by deleting portions of the Cas9 protein which are not well conserved or otherwise diverge within species within a family of Cas9. By reducing the size of the nucleic acid required to encode a functioning Cas9, additional nucleic acids can be included with a vector designed to deliver the Cas9, such as nucleic acids encoding guide RNA or regulatory elements or effector domains. If one uses the smallest characterized Cas9 family member, ~4,500 kilobases of DNA will be required to encode for the necessary genetic elements (Cas9 protein and gRNA) in order to properly localize Cas9 to the desired genomic locus. At 4,500 basepairs Cas9 is near the size limit for packaging within AAV based viral vector (which is a regulatory approved viral vector in Europe.) Further, some of the first transcriptional and epigenetic effector domains to be fused to programmable DNA binding proteins are greater than 2,000 basepairs and thus far out of the packaging limit for AAV vectors and approaching the limit of lentiviral packaging systems (~8,000 basepairs) once fused to Cas9.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

Mutant Cas9

To overcome the issues of large gene size encoding Cas9, a targeted deletion is carried out of various regions within one of the smallest characterized Cas9 family member NM-Cas9 (*Neisseria meningitides* Cas9). NM-Cas9 is 3,249 bp in size. Requirements for targeting to the genome and the residues involved in nuclease activity are determined. To generate versions of NM-Cas9 which are smaller in size, an alignment of Cas9 proteins was generated and contiguous stretches of low conservation were identified for deletion. Several regions of interest were identified and selectively removed from NM-Cas9 which was then assessed for function by using a Cas9 repressor assay. In the assay, a variant of NM-Cas9 was used that lacks nuclease activity but is able to be targeted to the 5' region of a reporter gene. If NM-Cas9 is able to bind to the reporter gene it will repress transcription and in the case of a fluorescent reporter, the cells will appear non-fluorescent.

Cas9 alignment and deletion prediction: Full length sequences of Cas9 homologs were obtained either from the PFAM database or from a database search such as jackHMMER (R. D. Finn, J. Clements, S. R. Eddy, Nucleic Acids Research (2011) Web Server Issue 39:W29-W37 hereby incorporated by reference in its entirety). In case the collection of sequences is not aligned, an alignment is created using an alignment algorithm such as CLUSTALW (Sievers F, Wilm A, Dineen D G, Gibson T J, Karplus K, Li W, Lopez R, McWilliam H, Remmert M, Soding J, Thompson J D, Higgins D G (2011) hereby incorporated by reference in its entirety), or equivalent. The alignment was computationally cut to the positions of the sequence of interest and conditioned to diminish alignment bias (e.g. sequences with a greater than 95% pairwise identity were removed). Conservation is calculated as the entropy or relative entropy of amino acid frequencies per position, taking into account the amount of amino acids and gaps at that position. Deletions are targeted towards regions of low conservation. In iterations with experimental verification, the deletions are expanded or shifted.

Deletion construction and characterization: Bacterial plasmids expressing nuclease null NM-Cas9 were previously generated as described in Esvelt, K. M., Mali, P., Braff, J. L., Moosburner, M., Yaung, S. J., and Church, G. M. (2013) *Nat Methods* 10, 1116-1121 hereby incorporated by reference in its entirety. To create targeted deletions within NM-Cas9, Gibson assembly was employed as described in Gibson, D. G., Young, L., Chuang, R. Y., Venter, J. C., Hutchison, C. A., 3rd, and Smith, H. O. (2009) *Nat Methods* 6, 343-345 hereby incorporated by reference in its entirety. Primers containing overlapping complementarily and which are designed to remove targeted regions within NM-Cas9 along with inserting a SGGGS linker were purchased and used in PCR reactions. PCR fragments were gel purified, assembled in vitro using Gibson assembly and transformed into *E. coli*. Clones were sequence verified and tested using a modified form of previously generated NM-Cas9 reporter plasmids (See (2013) *Nat Methods* 10, 1116-1121) in which a single plasmid (instead of two) contains the NM-Cas9 spacer, targeted protospacer and YFP reporter for NM-Cas9 activity. Briefly, in this assay cells are co-transformed with synthetic NM-Cas9 variants and the reporter plasmid. The doubly transformed cells are then grown up at 37° C., and the amount of YFP fluorescence is measured using a fluorescence plate reader and compared to cells that are transformed with a control plasmid with wild-type nuclease null NM-Cas9 and the reporter plasmid.

The below sequences are for the two largest NM-Cas9 single deletion mutants generated and the YFP reporter plasmid. The sequence of the SGGGS linker which replaces the deleted regions within NM-cas9 is shown in CAPS.

NM-Cas9-Δ255-449

[SEQ ID NO: 1]

```
atggccgccttcaagcccaacccatcaactacatcctgggcctggccatcggcatcgccagcgtgggctgggccatggtggagatcgacgaggacgagaa
ccccatctgcctgatcgacctgggtgtgcgcgtgttcgagcgcgctgaggtgcccaagactggtgacagtctggctatggctcgccggcttgctcgctctg
ttcggcgccttactcgccggcgcgctcaccgccttctgcgcgctcgccgcctgctgaagcgcgagggtgtgctgcaggctgccgacttcgacgagaacggc
ctgatcaagagcctgcccaacactccttggcagctgcgcgctgccgctctggaccgcaagctgactcctctggagtggagcgccgtgctgctgcacctgat
caagcaccgcggctacctgagccagcgcaagaacgagggcgagaccgccgacaaggagctgggtgctctgctgaagggcgtggccgacaacgcccacgccc
tgcagactggtgacttccgcactcctgctgagctggccctgaacaagttcgagaaggagagcggccacatccgcaaccagcgcggcgactacagccacacc
ttcagccgcaaggacctgcaggccgagctgatcctgctgttcgagaagcagaaggagttcggcaaccccacgtgagcggcggcctgaaggagggcatcga
gaccctgctgatgacccagcgccccgcctgagcggcgacgccgtgcagaagatgTCCGGCGGCGGTTCGggcgaccactacggcaagaagaacaccgagg
agaagatctacctgcctcctatccccgccgacgagatccgcaacccgtggtgctgcgcgccctgagccaggcccgcaaggtgatcaacggcgtggtgcgc
cgctacggcagccccgcccgcatccacatcgagaccgcccgcgaggtgggcaagagcttcaaggaccgcaaggagatcgagaagcgccaggaggagaaccg
caaggaccgcgagaaggccgccgccaagttccgcgagtacttccccaacttcgtgggcgagcccaagagcaaggacatcctgaagctgcgcctgtacgagc
agcagcacgcaagtgcctgtacagcggcaaggagatcaacctgggccgcctgaacgagaagggctacgtggagatcgccgctgccctgcccttcagccgc
acctgggacgacagcttcaacaacaaggtgctggtgctgggcagcgaggctcagaacaagggcaaccagaccccctacgagtacttcaacggcaaggacaa
cagccgcgagtggcaggagttcaaggcccgcgtggagaccagccgcttccccgcagcaagaagcagcgcatcctgctgcagaagttcgacgaggacggct
tcaaggagcgcaacctgaacgacacccgctacgtgaaccgcttcctgtgccagttcgtggccgaccgcatgcgcctgaccggcaagggcaagaagcgcgtg
ttcgccagcaacggccagatcaccaacctgctgcgcggcttctggggcctgcgcaaggtgcgcgccgagaacgaccgccaccacgccctggacgccgtggt
ggtggcctgcagcaccgtggccatgcagcagaagatcacccgcttcgtgcgctacaaggagatgaacgccttcgacggtaaaaccatcgacaaggagaccg
gcgaggtgctgcaccagaagacccacttcccccagccctgggagttcttcgcccaggaggtgatgatccgcgtgttcggcaagcccgacggcaagcccgag
ttcgaggaggccgacaccccgagaagctgcgcaccctgctggccgagaagctgagcagccgcctgaggccgtgcacgagtacgtgactcctctgttcgtg
agccgcgcccccaaccgcaagatgagcggtcagggtcacatggagaccgtgaagagcgccaagcgcctggacgagggcgtgagcgtgctgcgcgtgcccct
gacccagctgaagctgaaggacctggagaagatggtgaaccgcgagcgcgagcccaagctgtacgaggccctgaaggcccgcctggaggcccacaaggacg
accccgccaaggccttcgccgagcccttctacaagtacgacaaggccggcaaccgcacccagcaggtgaaggccgtgcgcgtggagcaggtgcagaagacc
ggcgtgtgggtgcgcaaccacaacggcatcgccgacaacgccaccatggtgcgcgtggacgtgttcgagaagggcgacaagtactacctggtgcccatcta
cagctggcaggtggccaagggcatcctgcccgaccgcgccgtggtgcagggcaaggacgaggaggactggcagctgatcgacgacagcttcaacttcaagt
tcagcctgcaccccaacgacctggtggaggtgatcaccaagaaggcccgcatgttcggctacttcgccagctgccaccgcggcaccggcaacatcaacatc
cgcatccacgacctggaccacaagatcggcaagaacggcatcctggagggcatcggcgtgaagaccgccctgagcttccagaagtaccagatcgacgagct
gggcaaggagatccgcccctgccgcctgaagaagcgccctcctgtgcgctaa
```

NM-Cas9-Δ567-654

[SEQ ID NO: 2]

```
atggccgccttcaagcccaacccatcaactacatcctgggcctggccatcggcatcgccagcgtgggctgggccatggtggagatcgacgaggacgagaa
ccccatctgcctgatcgacctgggtgtgcgcgtgttcgagcgcgctgaggtgcccaagactggtgacagtctggctatggctcgccggcttgctcgctctg
ttcggcgccttactcgccggcgcgctcaccgccttctgcgcgctcgccgcctgctgaagcgcgagggtgtgctgcaggctgccgacttcgacgagaacggc
ctgatcaagagcctgcccaacactccttggcagctgcgcgctgccgctctggaccgcaagctgactcctctggagtggagcgccgtgctgctgcacctgat
caagcaccgcggctacctgagccagcgcaagaacgagggcgagaccgccgacaaggagctgggtgctctgctgaagggcgtggccgacaacgcccacgccc
tgcagactggtgacttccgcactcctgctgagctggccctgaacaagttcgagaaggagagcggccacatccgcaaccagcgcggcgactacagccacacc
```

-continued ttcagccgcaaggacctgcaggccgagctgatcctgctgttcgagaagcagaaggagttcggcaaccccacgtgagcggcggcctgaaggagggcatcga gaccctgctgatgacccagcgccccgccctgagcggcgacgccgtgcagaagatgctgggccactgcaccttcgagccagccgagcccaaggccgccaaga acacctacaccgccgagcgcttcatctggctgaccaagctgaacaacctgcgcatcctggagcagggcagcgagcgcccctgaccgacaccgagcgcgcc accctgatggacgagccctaccgcaagagcaagctgacctacgcccaggcccgcaagctgctgggtctggaggacaccgccttcttcaagggcctgcgcta cggcaaggacaacgccgaggccagcaccctgatggagatgaaggcctaccacgccatcagccgcgccctggagaaggagggcctgaaggacaagaagagtc ctctgaacctgagccccgagctgcaggacgagatcggcaccgccttcagcctgttcaagaccgacgaggacatcaccggccgcctgaaggaccgcatccag cccgagatcctggaggccctgctgaagcacatcagcttcgacaagttcgtgcagatcagcctgaaggccctgcgccgcatcgtgcccctgatggagcaggg caagcgctacgacgaggcctgcgccgagatctacggcgaccactacggcaagaagaacaccgaggagaagatctacctgcctcctatccccgccgacgaga tccgcaaccccgtggtgctgcgcgccctgagccaggcccgcaaggtgatcaacggcgtggtgcgccgctacggcagccccgcccgcatccacatcgagacc gcccgcgaggtgggcaagagcttcaaggaccgcaaggagatcgagaagcgccaggaggagaaccgcaaggaccgcgagaaggccgccgccaagttccgcga gtacttccccaacttcgtgggcgagcccaagagcaaggacatcctgaagctgcgcctgtacgagcagcagcacgggcaagtgcTCCGGCGGCGGTTCGcaga agttcgacgaggacggcttcaaggagcgcaacctgaacgacacccgctacgtgaaccgcttcctgtgccagttcgtggccgaccgcatgcgcctgaccggc aagggcaagaagcgcgtgttcgccagcaacggccagatcaccaacctgctgcgcggcttctggggcctgcgcaaggtgcgcgccgagaacgaccgccacca cgccctggacgccgtggtggtggcctgcagcaccgtggccatgcagcagaagatcacccgcttcgtgcgctacaaggagatgaacgccttcgacggtaaaa ccatcgacaaggagaccggcgaggtgctgcaccagaagacccacttcccccagccctgggagttcttcgcccaggaggtgatgatccgcgtgttcggcaag cccgacggcaagcccgagttcgaggaggccgacaccccgagaagctgcgcaccctgctggccgagaagctgagcagccgccctgaggccgtgcacgagta cgtgactcctctgttcgtgagccgcgcccccaaccgcaagatgagcggtcagggtcacatggagaccgtgaagagcgccaagcgcctggacgagggcgtga gcgtgctgcgcgtgcccctgacccagctgaagctgaaggacctggagaagatggtgaaccgcgagcgcgagcccaagctgtacgaggccctgaaggcccgc ctggaggcccacaaggacgaccccgccaaggccttcgccgagcccttctacaagtacgacaaggccggcaaccgcacccagcaggtgaaggccgtgcgcgt ggagcaggtgcagaagaccggcgtgtgggtgcgcaaccacaacggcatcgccgacaacgccaccatggtgcgcgtggacgtgttcgagaagggcgacaagt actacctggtgcccatctacagctggcaggtggccaagggcatcctgcccgaccgcgccgtggtgcagggcaaggacgaggaggactggcagctgatcgac gacagcttcaacttcaagttcagcctgcaccccaacgacctggtggaggtgatcaccaagaaggcccgcatgttcggctacttcgccagctgccaccgcgg caccggcaacatcaacatccgcatccacgacctggaccacaagatcggcaagaacggcatcctggagggcatcggcgtgaagaccgccctgagcttccaga agtaccagatcgacgagctgggcaaggagatccgcccctgccgcctgaagaagcgccctcctgtgcgctaa YFP reporter plasmid

[SEQ ID NO: 3]

agctctcgaaccccagagtcccgctcagaagaactcgtcaagaaggcgatagaaggcgatgcgctgcgaatcgggagcggcgataccgtaaagcacgagga agcggtcagcccattcgccgccaagctcttcagcaatatcacgggtagccaacgctatgtcctgatagcggtccgccacacccagccggccacagtcgatg aatccagaaaagcggccattttccaccatgatattcggcaagcaggcatcgccatgggtcacgacgagatcctcgccgtcgggcatgcgcgccttgagcct ggcgaacagttcggctggcgcgagcccctgatgctcttcgtccagatcatcctgatcgacaagaccggcttccatccgagtacgtgctcgctcgatgcgat gtttcgcttggtggtcgaatgggcaggtagccggatcaagcgtatgcagccgccgcattgcatcagccatgatggatactttctcggcaggagcaaggtga gatgacaggagatcctgccccggcacttcgcccaatagcagccagtcccttcccgcttcagtgacaacgtcgagcacagctgcgcaaggaacgcccgtcgt ggccagccacgatagccgcgctgcctcgtcctgcagttcattcagggcaccggacaggtcggtcttgacaaaaagaaccgggcgcccctgcgctgacagcc ggaacacggcggcatcagagcagccgattgtctgttgtgcccagtcatagccgaatagcctctccacccaagcggccggagaacctgcgtgcaatccatct tgttcaatcatgcgaaacgatcctcatcctgtctcttgatcagatcttgatccctgcgccatcagatccttggcggcaagaaagccatccagtttacttt gcagggcttcccaaccttaccagagggcgccccagctggcaattccgacgtctaagaaaccattattatcatgacattaacctataaaaataggcgtatca cgaggccctttcgtcttcacctcgaggggacaatgaaaacgttagtcatggcgcgccttgacggctagctcagtcctaggtacagtgctagcttaatgctc gcacatagcagaactttaaaagtattcgccatgttgtagctcccttttctcatttcgcagtgctacaatccgccgctatggtcccacgtagagcatacgaa aaaaagtcaaaagcctccgaccggaggtcggccttacttgctagcagagtttgtagaaacgcaaaaaggccatccgtcaggatggccctctgcttaatttg atgcctggcagtttatggcgggcgtcctgcccgccaccctccgggccgttgcttcgcaacgttcaaatccgctcccggcggtttgtcctactcaggagagc gttcaccgacaaacaacagataaaacgaaaggcccagtctttcgactgagcctttcgttttatttgatgcctggcagttccctactctcgcatggggagac cccacactaccatcggcgctacggcgtttcacttctgagttcggcatggggtcaggtgggaccaccgcgctactgccgccaggcaaattctgttttatcag -continued

```
accgcttctgcgttctgatttaatctgtatcaggctgaaaatcttctctcatccgccaaaacagccccgtagaaaaagggacgttgatcggcacgtaagag gttccacgataaatatctaacaccgtgcgtgttgactattttacctctggcggtgataatggttgcatgtactagaattctttaactttaagaaggagata tacatatgaatccctatggcgaatactttaaagtctcgtaaaggagaagaacttttcactggagttgtcccaattcttgttgaattagatggtgatgtt aatgggcacaaattttctgtcagtggagagggtgaaggtgatgcaacatacggaaaacttacccttaaattttatttgcactactggaaaactacctgttcc atggccaacacttgtcactactttcggttatggtctaaaatgctttgctagatacccagatcatatgaaacggcatgacttttcaagagtgccatgcccg aaggttatgtacaggaaagaactatattttcaaagatgacgggaactacaagacacgtgctgaagtcaagtttgaaggtgataccttgttaatagaatc gagttaaaaggtattgattttaaagaagatggaaacattcttggacacaaattggaatacaactataactcacacaatgtatacatcatggcagacaaaca aaagaatggaatcaaagttaacttcaaaattagacacaacattgaagatggaagcgttcaactagcagaccattatcaacaaaatactccaattggcgatg gccctgtccttttaccagacaaccattacctgtcctatcaatctgccctttcgaaagatcccaacgaaaagagagaccacatggtccttcttgagtttgta acagctgctgggattacacatggcatggatgaactatacaaataagcttaaccgaagcgtttgatagttgatatcctttgcctgcggccgcaactagaggc atcaaataaaacgaaaggctcagtcgaaagactgggcctttcgttttatctgttgtttgtcggtgaacgctctcctgagtaggacaaatccgccgccctag acctagggtacgggttttgctgcccgcaaacgggctgttctggtgttgctagtttgttatcagaatcgcagatccggcttcaggtttgccggctgaaagcg ctatttcttccagaattgccatgattttttccccacgggaggcgtcactggctcccgtgttgtcggcagctttgattcgataagcagcatcgcctgtttca ggctgtctatgtgtgactgttgagctgtaacaagttgtctcaggtgttcaatttcatgttctagttgctttgttttactggtttcacctgttctattaggt gttacatgctgttcatctgttacattgtcgatctgttcatggtgaacagctttaaatgcaccaaaaactcgtaaaagctctgatgtatctatcttttttac accgttttcatctgtgcatatggacagttttccctttgatatctaacggtgaacagttgttctacttttgtttgttagtcttgatgcttcactgatagata caagagccataagaacctcagatccttccgtatttagccagtatgttctctagtgtggttcgttgtttttgcgtgagccatgagaacgaaccattgagatc atgcttactttgcatgtcactcaaaaattttgcctcaaaactggtgagctgaattttttgcagttaaagcatcgtgtagtgtttttcttagtccgttacgta ggtaggaatctgatgtaatggttgttggtattttgtcaccattcatttttatctggttgttctcaagttcggttacgagatccatttgtctatctagttca acttggaaaatcaacgtatcagtcgggcggcctcgcttatcaaccaccaatttcatattgctgtaagtgtttaaatctttacttattggtttcaaaaccca ttggttaagcctttaaaactcatggtagttattttcaagcattaacatgaacttaaattcatcaaggctaatctctatatttgccttgtgagttttctttt gtgttagttcttttaataaccactcataaatcctcatagagtatttgttttcaaaagacttaacatgttccagattatattttatgaatttttttaactgg aaaagataaggcaatatctcttcactaaaaactaattctaattttcgcttgagaacttggcatagtttgtccactggaaaatctcaaagcctttaaccaa aggattcctgatttccacagttctcgtcatcagctctctggttgctttagctaatacaccataagcattttccctactgatgttcatcatctgagcgtatt ggttataagtgaacgataccgtccgttctttccttgtagggttttcaatcgtggggttgagtagtgccacacagcataaaattagcttggtttcatgctcc gttaagtcatagcgactaatcgctagttcatttgctttgaaaacaactaattcagacatacatctcaattggtctaggtgattttaatcactataccaatt gagatgggctagtcaatgataattactagtcctttccctttgagttgtgggtatctgtaaattctgctagacctttgctggaaaacttgtaaattctgcta gaccctctgtaaattccgctagacctttgtgtgttttttttgtttatattcaagtggttataatttataagaataagaaagaataaaaaaagataaaaaga atagatcccagccctgtgtataactcactactttagtcagttccgcagtattacaaaaggatgtcgcaaacgctgtttgctcctctacaaaacagaccta aaaccctaaaggcttaagtagcaccctcgcaagctcgggcaaatcgctgaatattccttttgtctccgaccatcaggcacctgagtcgctgtcttttcgt gacattcagttcgctgcgctcacggctctggcagtgaatgggggtaaatggcactacaggcgccttttatggattcatgcaaggaaactacccataataca agaaaagcccgtcacgggcttctcagggcgttttatggcgggtctgctatgtggtgctatctgacttttttgctgttcagcagttcctgccctctgattttc cagtctgaccacttcggattatcccgtgacaggtcattcagactggctaatgcacccagtaaggcagcggtatcatcaacaggcttacccgtcttactgtc cctagtgcttggattacaccaataaaaaacgcccggcggcaaccgagcgttctgaacaaatccagatggagttctgaggtcattactggatctatcaacag gagtccaagcg.
```

According to the methods described herein, several deletions within NM-Cas9 have been identified, the largest NM-Cas9-Δ255-449 removes 595 basepairs and shows only a 16% decrease in activity as measured by the reporter assay (See FIG. 1). According to certain aspects, mutant Cas9 proteins are provided which have 1000 fewer base pairs compared to the wild type Cas9, such as NM-Cas9 and retain near wild-type levels of activity.

EXAMPLE II

Targeting Cas9 Nuclease Domains for Deletion

Along with targeting regions of low sequence conservation in the case where a nickase or nuclease null allele of Cas9 is desired, one can target the Cas9 nuclease domains along with their surrounding nucleotides for deletion. Utilizing such an approach, a functional NM-Cas9 allele lacking the HNH motif and surrounding nucleotides NM-Cas9-Δ567-654 was made which retained near wild-type ability to bind DNA as determined by the YFP reporter assay.

EXAMPLE III

Methods to Construct a Non-Biased NM-Cas9 Deletion Library

Aside from taking a targeted approach to generating Cas9 deletions, aspects of the present disclosure include a high-throughput approach for random deletion creation and screening of functional mutants. According to an exemplary method, plasmid DNA containing the desired Cas9 allele can be sheared using a promiscuous nuclease, sonication, repeatedly pipetting the sample, or other chemical, enzymatic or environmental means. Once fragmented, the plasmid DNA can be treated with exonucleases to remove nucleotides from the Cas9 gene. After exonuclease treatment, fragmented ends are made blunt ended with enzymes such as Mung Bean nuclease or Klenow polymerase and ligated together to regenerate a Cas9 plasmid containing a random deletion. To insert an exogenous domain such as a linker or effector motif within the deleted portion of Cas9, such domains can be ligated to the blunt ended fragmented DNA, and subsequent circularization of the plasmid will produce a Cas9 coding sequence where the exogenous domain has been inserted within the deleted portion of Cas9. The library of circularized molecules will then be transformed into *E. coli* and plasmid DNA will be extracted. At this point, the library can be transformed into cells containing a reporter assay for Cas9 activity and members of the library that maintain functional activity can be identified. Alternatively, to reduce the size of the library to be screened, the coding sequence for Cas9 from the newly generated library can be isolated via digestion or PCR and the fragments can be size-selected to be shorter than the initial wild-type Cas9 gene. These smaller members can then be ligated back into the starting vector and transformed into cells containing the reporter of Cas9 activity.

Aside from plasmid shearing, a library of oligonucleotides can be generated that have 3' homology to the Cas9 gene but contain 5' homology to each other, where the 3' end of each oligonucleotide binds to a different stretch of around 30 basepairs within Cas9. These oligonucleotides cover both the sense and anti-sense strands of the Cas9 coding sequence. PCR can then be performed with these oligonucleotides to generate a series of Cas9 fragments with each product from a given sense PCR reaction having complementarity to all other anti-sense PCR products and vice-versa. These fragments can then be annealed together using methods such as Gibson assembly or overlap extension PCR followed by ligation into a vector backbone and transformed into cells, generating a library of Cas9 variants with random stretches of the Cas9 gene removed. For longer linkers or to insert an effector domain within the deleted regions, the oligonucleotides on their 5' ends should contain complementarity towards the longer linker or effector domain and this domain should then be included in the Gibson assembly reaction or during overlap extension PCR. Once a library has been generated, functional variants can be identified using a reporter assay such as the YFP reporter system described herein.

The invention claimed is:

1. A method of making a mutant Cas9 protein having DNA binding activity comprising
aligning full length amino acid sequences of a family of Cas9 proteins,
identifying one or more diverging amino acid sequence portions among the full length amino acid sequences of the family of Cas9 proteins,
identifying a nucleic acid sequence for the one or more diverging amino acid sequences portions,
generating a nucleic acid sequence for a target Cas9 protein which lacks the nucleic acid sequence for the one or more diverging amino acid sequences portions, and
generating a mutant Cas9 protein from the generated nucleic acid sequence.

2. The method of claim 1 wherein the target Cas9 protein has nuclease activity.

3. The method of claim 1 wherein the target Cas9 protein is a nickase.

4. The method of claim 1 wherein the target Cas9 protein is nuclease null.

5. The method of claim 1 wherein the nucleic acid sequence encoding the one or more diverging amino acid sequences portions is deleted from a nucleic acid sequence encoding a full length Cas9 protein.

6. The method of claim 1 wherein the nucleic acid sequence encoding the one or more diverging amino acid sequences portions is deleted from a nucleic acid sequence encoding a full length Cas9 protein and replaced with a linker.

7. The method of claim 1 wherein the nucleic acid sequence encoding the one or more diverging amino acid sequences portions is deleted from a nucleic acid sequence encoding the target Cas9 protein and replaced with a SGGGS linker.

8. The method of claim 1 wherein the mutant Cas9 protein is a mutant Cas9 protein encoded by the nucleic acid sequence of SEQ ID NO:1.

9. The method of claim 1 wherein the mutant Cas9 protein is a mutant Cas9 protein encoded by the nucleic acid sequence of SEQ ID NO:2.

* * * * *

SEQUENCE LISTING

```
<160> NUMBER OF SEQ ID NOS: 3

<210> SEQ ID NO 1
<211> LENGTH: 2679
<212> TYPE: DNA
<213> ORGANISM: Artificial
<220> FEATURE:
<223> OTHER INFORMATION: Cas9 deletion mutant

<400> SEQUENCE: 1
atggccgcct tcaagcccaa ccccatcaac tacatcctgg gcctggccat cggcatcgcc      60
agcgtgggct gggccatggt ggagatcgac gaggacgaga accccatctg cctgatcgac     120
ctgggtgtgc gcgtgttcga gcgcgctgag gtgcccaaga ctggtgacag tctggctatg     180
gctcgccggc ttgctcgctc tgttcggcgc cttactcgcc ggcgcgctca ccgccttctg     240
cgcgctcgcc gcctgctgaa gcgcgagggt gtgctgcagg ctgccgactt cgacgagaac     300
ggcctgatca agagcctgcc caacactcct ggcagctgc gcgctgccgc tctggaccgc      360
aagctgactc ctctggagtg gagcgccgtg ctgctgcacc tgatcaagca ccgcggctac     420
ctgagccagc gcaagaacga gggcgagacc gccgacaagg agctgggtgc tctgctgaag     480
ggcgtggccg acaacgccca cgccctgcag actggtgact tccgcactcc tgctgagctg     540
gccctgaaca agttcgagaa ggagagcggc cacatccgca accagcgcgg cgactacagc     600
cacaccttca gccgcaagga cctgcaggcc gagctgatcc tgctgttcga gaagcagaag     660
gagttcggca accccacgt gagcggcggc ctgaaggagg gcatcgagac cctgctgatg      720
acccagcgcc ccgccctgag cggcgacgcc gtgcagaaga tgtccggcgg cggttcgggc     780
gaccactacg gcaagaagaa caccgaggag aagatctacc tgcctcctat ccccgccgac     840
```

-continued

```
gagatccgca accccgtggt gctgcgcgcc ctgagccagg cccgcaaggt gatcaacggc    900
gtggtgcgcc gctacggcag ccccgcccgc atccacatcg agaccgcccg cgaggtgggc    960
aagagcttca aggaccgcaa ggagatcgag aagcgccagg aggagaaccg caaggaccgc   1020
gagaaggccg ccgccaagtt ccgcgagtac ttccccaact tcgtgggcga gcccaagagc   1080
aaggacatcc tgaagctgcg cctgtacgag cagcagcacg gcaagtgcct gtacagcggc   1140
aaggagatca acctgggccg cctgaacgag aagggctacg tggagatcgc cgctgccctg   1200
cccttcagcc gcacctggga cgacagcttc aacaacaagg tgctggtgct gggcagcgag   1260
gctcagaaca agggcaacca gacccctac gagtacttca cggcaagga caacagccgc   1320 gagtggcagg agttcaaggc ccgcgtggag accagccgct cccccgcag caagaagcag   1380 cgcatcctgc tgcagaagtt cgacgaggac ggcttcaagg agcgcaacct gaacgacacc   1440
cgctacgtga accgcttcct gtgccagttc gtggccgacc gcatgcgcct gaccggcaag   1500
ggcaagaagc gcgtgttcgc cagcaacggc cagatcacca acctgctgcg cggcttctgg   1560
ggcctgcgca aggtgcgcgc cgagaacgac cgccaccacg ccctggacgc cgtggtggtg   1620
gcctgcagca ccgtggccat gcagcagaag atcacccgct tcgtgcgcta caaggagatg   1680
aacgccttcg acggtaaaac catcgacaag gagaccggcg aggtgctgca ccagaagacc   1740
cacttccccc agccctggga gttcttcgcc caggaggtga tgatccgcgt gttcggcaag   1800
cccgacggca agcccgagtt cgaggaggcc gacacccccg agaagctgcg caccctgctg   1860
gccgagaagc tgagcagccg ccctgaggcc gtgcacgagt acgtgactcc tctgttcgtg   1920
agccgcgccc ccaaccgcaa gatgagcggt cagggtcaca tggagaccgt gaagagcgcc   1980
aagcgcctgg acgagggcgt gagcgtgctg cgcgtgcccc tgacccagct gaagctgaag   2040
gacctggaga agatggtgaa ccgcgagcgc gagcccaagc tgtacgaggc cctgaaggcc   2100
cgcctggagg cccacaagga cgaccccgcc aaggccttcg ccgagcccct ctacaagtac   2160
gacaaggccg gcaaccgcac ccagcaggtg aaggccgtgc gcgtggagca ggtgcagaag   2220
accggcgtgt gggtgcgcaa ccacaacggc atcgccgaca cgccaccat ggtgcgcgtg   2280 gacgtgttcg agaagggcga caagtactac ctggtgccca tctacagctg gcaggtggcc   2340
aagggcatcc tgcccgaccg cgccgtggtg cagggcaagg acgaggagga ctggcagctg   2400
atcgacgaca gcttcaactt caagttcagc ctgcacccca cgacctggt ggaggtgatc   2460 accaagaagg cccgcatgtt cggctacttc gccagctgcc accgcggcac cggcaacatc   2520
aacatccgca tccacgacct ggaccacaag atcggcaaga acggcatcct ggagggcatc   2580
ggcgtgaaga ccgccctgag cttccagaag taccagatcg acgagctggg caaggagatc   2640
cgcccctgcc gcctgaagaa cgccctcct gtgcgctaa                           2679
```

<210> SEQ ID NO 2
<211> LENGTH: 3000
<212> TYPE: DNA
<213> ORGANISM: Artificial
<220> FEATURE:
<223> OTHER INFORMATION: Cas9 deletion mutant

<400> SEQUENCE: 2

```
atggccgcct tcaagcccaa ccccatcaac tacatcctgg gcctggccat cggcatcgcc     60
agcgtgggct gggccatggt ggagatcgac gaggacgaga accccatctg cctgatcgac    120
ctgggtgtgc gcgtgttcga gcgcgctgag gtgcccaaga ctggtgacag tctggctatg    180
```

-continued

```
gctcgccggc ttgctcgctc tgttcggcgc cttactcgcc ggcgcgctca ccgccttctg      240
cgcgctcgcc gcctgctgaa gcgcgagggt gtgctgcagg ctgccgactt cgacgagaac      300
ggcctgatca agagcctgcc caacactcct tggcagctgc gcgctgccgc tctggaccgc      360
aagctgactc ctctggagtg gagcgccgtg ctgctgcacc tgatcaagca ccgcggctac      420
ctgagccagc gcaagaacga gggcgagacc gccgacaagg agctgggtgc tctgctgaag      480
ggcgtggccg acaacgccca cgccctgcag actggtgact ccgcactcc tgctgagctg      540 gccctgaaca agttcgagaa ggagagcggc cacatccgca accagcgcgg cgactacagc      600
cacaccttca gccgcaagga cctgcaggcc gagctgatcc tgctgttcga aagcagaag      660 gagttcggca ccccccacgt gagcggcggc ctgaaggagg catcgagac cctgctgatg      720 acccagcgcc ccgccctgag cggcgacgcc gtgcagaaga tgctgggcca ctgcaccttc      780
gagccagccg agcccaaggc cgccaagaac acctacaccg ccgagcgctt catctggctg      840
accaagctga caacctgcg catcctggag cagggcagcg agcgcccct gaccgacacc      900 gagcgcgcca ccctgatgga cgagccctac cgcaagagca agctgaccta cgcccaggcc      960
cgcaagctgc tgggtctgga ggacaccgcc ttcttcaagg gcctgcgcta cggcaaggac     1020
aacgccgagg ccagcaccct gatggagatg aaggcctacc acgccatcag ccgcgccctg     1080
gagaaggagg gcctgaagga caagaagagt cctctgaacc tgagccccga gctgcaggac     1140
gagatcggca ccgccttcag cctgttcaag accgacgagg acatcaccgg ccgcctgaag     1200
gaccgcatcc agcccgagat cctggaggcc ctgctgaagc acatcagctt cgacaagttc     1260
gtgcagatca gcctgaaggc cctgcgccgc atcgtgcccc tgatggagca gggcaagcgc     1320
tacgacgagg cctgcgccga gatctacggc gaccactacg gcaagaagaa caccgaggag     1380
aagatctacc tgcctcctat ccccgccgac gagatccgca ccccgtggt gctgcgcgcc     1440 ctgagccagg cccgcaaggt gatcaacggc gtggtgcgcc gctacggcag ccccgcccgc     1500
atccacatcg agaccgcccg cgaggtgggc aagagcttca aggaccgcaa ggagatcgag     1560
aagcgccagg aggagaaccg caaggaccgc gagaaggccg ccgccaagtt ccgcgagtac     1620
ttccccaact tcgtgggcga gcccaagagc aaggacatcc tgaagctgcg cctgtacgag     1680
cagcagcacg gcaagtgctc cggcggcggt tcgcagaagt tcgacgagga cggcttcaag     1740
gagcgcaacc tgaacgacac ccgctacgtg aaccgcttcc tgtgccagtt cgtggccgac     1800
cgcatgcgcc tgaccggcaa gggcaagaag cgcgtgttcg ccagcaacgg ccagatcacc     1860
aacctgctgc gcggcttctg gggcctgcgc aaggtgcgcg ccgagaacga ccgccaccac     1920
gccctggacg ccgtggtggt ggcctgcagc accgtggcca tgcagcagaa gatcacccgc     1980
ttcgtgcgct acaaggagat gaacgccttc gacggtaaaa ccatcgacaa ggagaccggc     2040
gaggtgctgc accagaagac ccacttcccc cagccctggg agttcttcgc ccaggaggtg     2100
atgatccgcg tgttcggcaa gcccgacggc aagcccgagt cgaggaggc cgacacccc     2160 gagaagctgc gcaccctgct ggccgagaag ctgagcagcc gccctgaggc cgtgcacgag     2220
tacgtgactc ctctgttcgt gagccgcgcc cccaaccgca agatgagcgg tcagggtcac     2280
atggagaccc tgaagagcgc caagcgcctg gacgagggct gagcgtgct gcgcgtgccc     2340 ctgacccagc tgaagctgaa ggacctggag aagatggtga accgcgagcg cgagcccaag     2400
ctgtacgagg ccctgaaggc ccgcctggag gcccacaagg acgacccgc caaggccttc     2460 gccgagcccct tctacaagta cgacaaggcc ggcaaccgca cccagcaggt gaaggccgtg     2520
cgcgtggagc aggtgcagaa gaccggcgtg tgggtgcgca accacaacgg catcgccgac     2580
```

```
aacgccacca tggtgcgcgt ggacgtgttc gagaagggcg acaagtacta cctggtgccc    2640
atctacagct ggcaggtggc caagggcatc ctgcccgacc gcgccgtggt gcagggcaag    2700
gacgaggagg actggcagct gatcgacgac agcttcaact tcaagttcag cctgcacccc    2760
aacgacctgg tggaggtgat caccaagaag gcccgcatgt tcggctactt cgccagctgc    2820
caccgcggca ccggcaacat caacatccgc atccacgacc tggaccacaa gatcggcaag    2880
aacggcatcc tggagggcat cggcgtgaag accgccctga gcttccagaa gtaccagatc    2940
gacgagctgg gcaaggagat ccgccccctgc cgcctgaaga agcgccctcc tgtgcgctaa    3000
```

<210> SEQ ID NO 3
<211> LENGTH: 5064
<212> TYPE: DNA
<213> ORGANISM: Artificial
<220> FEATURE:
<223> OTHER INFORMATION: Cas9 deletion mutant

<400> SEQUENCE: 3

```
agctctcgaa ccccagagtc ccgctcagaa gaactcgtca agaaggcgat agaaggcgat      60
gcgctgcgaa tcgggagcgg cgataccgta agcacgagg aagcggtcag cccattcgcc     120
gccaagctct tcagcaatat cacgggtagc caacgctatg tcctgatagc ggtccgccac     180
acccagccgg ccacagtcga tgaatccaga aaagcggcca ttttccacca tgatattcgg     240
caagcaggca tcgccatggg tcacgacgag atcctcgccg tcgggcatgc gcgccttgag     300
cctggcgaac agttcggctg gcgcgagccc ctgatgctct tcgtccagat catcctgatc     360
gacaagaccg gcttccatcc gagtacgtgc tcgctcgatg cgatgtttcg cttggtggtc     420
gaatgggcag gtagccggat caagcgtatg cagccgccgc attgcatcag ccatgatgga     480
tactttctcg gcaggagcaa ggtgagatga caggagatcc tgccccggca cttcgcccaa     540
tagcagccag tcccttcccg cttcagtgac aacgtcgagc acagctgcgc aaggaacgcc     600
cgtcgtggcc agccacgata gccgcgctgc ctcgtcctgc agttcattca gggcaccgga     660
caggtcggtc ttgacaaaaa gaaccgggcg cccctgcgct gacagccgga acacggcggc     720
atcagagcag ccgattgtct gttgtgccca gtcatagccg aatagcctct ccacccaagc     780
ggccggagaa cctgcgtgca atccatcttg ttcaatcatg cgaaacgatc ctcatcctgt     840
ctcttgatca gatcttgatc ccctgcgcca tcagatcctt ggcggcaaga agccatcca     900 gtttactttg cagggcttcc caaccttacc agagggcgcc ccagctggca attccgacgt     960
ctaagaaacc attattatca tgacattaac ctataaaaat aggcgtatca cgaggccctt    1020
tcgtcttcac ctcgagggga caatgaaaac gttagtcatg gcgcgccttg acggctagct    1080
cagtcctagg tacagtgcta gcttaatgct cgcacatagc agaactttaa agtattcgc    1140 catgttgtag ctcccttct catttcgcag tgctacaatc cgccgctatg tcccacgta    1200 gagcatacgg aaaaaaagt caaaagcctc gaccgagg tcggcttac ttgctagcag    1260 agtttgtaga acgcaaaaa ggccatccgt caggatggcc ttctgcttaa tttgatgcct    1320
ggcagtttat gcgggcgtc ctgcccgcca cctccgggc cgttgcttcg caacgttcaa    1380
atccgctccc ggcggatttg tcctactcag gagagcgttc accgacaaac aacagataaa    1440
acgaaaggcc cagtctttcg actgagcctt tcgttttatt tgatgcctgg cagttcccta    1500
ctctcgcatg gggagacccc acactaccat cggcgctacg gcgtttcact tctgagttcg    1560
gcatggggtc aggtgggacc accgcgctac tgccgccagg caaattctgt tttatcagac    1620
```

```
cgcttctgcg ttctgattta atctgtatca ggctgaaaat cttctctcat ccgccaaaac    1680
agccccgtag aaaagggac gttgatcggc acgtaagagg ttccacgata aatatctaac    1740
accgtgcgtg ttgactattt tacctctggc ggtgataatg gttgcatgta ctagaattct    1800
ttaactttaa gaaggagata tacatatgaa tccectatgg cgaatacttt taaagtctcg    1860
taaaggagaa gaacttttca ctggagttgt cccaattctt gttgaattag atggtgatgt    1920
taatgggcac aaattttctg tcagtggaga gggtgaaggt gatgcaacat acggaaaact    1980 taccettaaa tttatttgca ctactggaaa actacctgtt ccatggccaa cacttgtcac    2040
tactttcggt tatggtctaa aatgctttgc tagatacccca gatcatatga aacggcatga    2100 cttttttcaag agtgccatgc ccgaaggtta tgtacaggaa agaactatat ttttcaaaga    2160
tgacgggaac tacaagacac gtgctgaagt caagtttgaa ggtgataccc ttgttaatag    2220
aatcgagtta aaaggtattg attttaaaga agatggaaac attcttggac acaaattgga    2280
atacaactat aactcacaca atgtatacat catggcagac aaacaaaaga atggaatcaa    2340
agttaacttc aaaattagac acaacattga agatggaagc gttcaactag cagaccatta    2400
tcaacaaaat actccaattg gcgatggccc tgtccttta ccagacaacc attacctgtc    2460
ctatcaatct gccctttcga aagatcccaa cgaaaagaga gaccacatgg tccttcttga    2520
gtttgtaaca gctgctggga ttacacatgg catggatgaa ctatacaaat aagcttaacc    2580
gaagcgtttg atagttgata tcctttgcct gcggccgcaa ctagaggcat caaataaaac    2640
gaaaggctca gtcgaaagac tgggcctttc gttttatctg ttgtttgtcg gtgaacgctc    2700
tcctgagtag gacaaatccg ccgccctaga cctaggtac gggttttgct gcccgcaaac    2760
gggctgttct ggtgttgcta gtttgttatc agaatcgcag atccggcttc aggtttgccg    2820
gctgaaagcg ctatttcttc cagaattgcc atgattttt ccccacggga ggcgtcactg    2880
gctcccgtgt tgtcggcagc tttgattcga taagcagcat cgcctgtttc aggctgtcta    2940
tgtgtgactt tgagctgta acaagttgtc tcaggtgttc aatttcatgt tctagttgct    3000
ttgttttact ggtttcacct gttctattag gtgttacatg ctgttcatct gttacattgt    3060
cgatctgttc atggtgaaca gctttaaatg caccaaaaac tcgtaaaagc tctgatgtat    3120
ctatcttttt tacaccgttt tcatctgtgc atatggacag ttttccctt gatatctaac    3180 ggtgaacagt tgttctactt tgttttgtta gtcttgatgc ttcactgata gatacaagag    3240
ccataagaac ctcagatcct tccgtattta gccagtatgt tctctagtgt ggttcgttgt    3300
ttttgcgtga gccatgagaa cgaaccattg agatcatgct tactttgcat gtcactcaaa    3360
aattttgcct caaaactggt gagctgaatt tttgcagtta aagcatcgtg tagtgttttt    3420
cttagtccgt tacgtaggta ggaatctgat gtaatggttg ttggtatttt gtcaccattc    3480
atttttatct ggttgttctc aagttcggtt acgagatcca tttgtctatc tagttcaact    3540
tggaaaatca acgtatcagt cgggcggcct cgcttatcaa ccaccaattt catattgctg    3600
taagtgttta aatctttact tattggttc aaaacccatt ggttaagcct tttaaactca    3660
tggtagttat tttcaagcat taacatgaac ttaaattcat caaggctaat ctctatattt    3720
gccttgtgag ttttctttg tgttagttct tttaataacc actcataaat cctcatagag    3780
tatttgtttt caaaagactt aacatgttcc agattatatt ttatgaattt ttttaactgg    3840
aaaagataag gcaatatctc ttcactaaaa actaattcta attttcgct tgagaacttg    3900 gcatagtttg tccactggaa aatctcaaag ccttttaacca aaggattcct gatttccaca    3960
gttctcgtca tcagctctct ggttgcttta gctaatacac cataagcatt ttccctactg    4020
```

-continued

```
atgttcatca tctgagcgta ttggttataa gtgaacgata ccgtccgttc tttccttgta    4080
gggttttcaa tcgtggggtt gagtagtgcc acacagcata aaattagctt ggtttcatgc    4140
tccgttaagt catagcgact aatcgctagt tcatttgctt tgaaaacaac taattcagac    4200
atacatctca attggtctag gtgattttaa tcactatacc aattgagatg ggctagtcaa    4260
tgataattac tagtccttttt cctttgagtt gtgggtatct gtaaattctg ctagacctt    4320 gctggaaaac ttgtaaattc tgctagaccc tctgtaaatt ccgctagacc tttgtgtgtt    4380 tttttttgttt atattcaagt ggttataatt tatagaataa agaaagaata aaaaaagata    4440
aaaagaatag atcccagccc tgtgtataac tcactactt agtcagttcc gcagtattac     4500
aaaaggatgt cgcaaacgct gtttgctcct ctacaaaaca gaccttaaaa ccctaaaggc    4560
ttaagtagca ccctcgcaag ctcgggcaaa tcgctgaata ttccttttgt ctccgaccat    4620
caggcacctg agtcgctgtc ttttcgtga cattcagttc gctgcgctca cggctctggc     4680
agtgaatggg ggtaaatggc actacaggcg cctttttatgg attcatgcaa ggaaactacc   4740
cataatacaa gaaaagcccg tcacgggctt ctcagggcgt tttatggcgg gtctgctatg    4800
tggtgctatc tgacttttg ctgttcagca gttcctgccc tctgattttc cagtctgacc     4860
acttcggatt atcccgtgac aggtcattca gactggctaa tgcacccagt aaggcagcgg    4920
tatcatcaac aggcttaccc gtcttactgt ccctagtgct tggattctca ccaataaaaa    4980
acgcccggcg gcaaccgagc gttctgaaca aatccagatg gagttctgag gtcattactg    5040
gatctatcaa caggagtcca agcg                                           5064
```